(12) United States Patent
Sankey et al.

(10) Patent No.: US 10,450,411 B2
(45) Date of Patent: Oct. 22, 2019

(54) COPOLYESTERIMIDES COMPRISING BIS(2-HYDROXYALKYL)-2,2'-(1,4-PHENYLENE)BIS(1,3-DIOXOISOINDOLINE-5-CARBOXYLATE) AND ARTICLES MADE THEREFROM

(71) Applicant: DUPONT TEIJIN FILMS U.S. LIMITED PARTNERSHIP, Chester, VA (US)

(72) Inventors: Stephen William Sankey, Redcar (GB); David Turner, Redcar (GB); Howard Colquhoun, Reading (GB); Stephen Jones, Reading (GB)

(73) Assignee: DUPONT TEIJIN FILMS U.S. LIMITED PARTNERSHIP, Chester, VA (US)

( * ) Notice: Subject to any disclaimer, the term of this patent is extended or adjusted under 35 U.S.C. 154(b) by 0 days.

(21) Appl. No.: 15/315,567

(22) PCT Filed: Jun. 19, 2015

(86) PCT No.: PCT/GB2015/051795
§ 371 (c)(1),
(2) Date: Dec. 1, 2016

(87) PCT Pub. No.: WO2015/193682
PCT Pub. Date: Dec. 23, 2015

(65) Prior Publication Data
US 2017/0174831 A1    Jun. 22, 2017

(30) Foreign Application Priority Data

Jun. 20, 2014 (GB) .................................. 1411044.9

(51) Int. Cl.
| | |
|---|---|
| C08G 63/685 | (2006.01) |
| C07D 209/48 | (2006.01) |
| C08G 73/10 | (2006.01) |
| C08G 73/16 | (2006.01) |
| D01F 6/84 | (2006.01) |
| C08J 5/18 | (2006.01) |

(52) U.S. Cl.
CPC ........ C08G 63/6856 (2013.01); C07D 209/48 (2013.01); C08G 73/1067 (2013.01); C08G 73/16 (2013.01); C08J 5/18 (2013.01); D01F 6/84 (2013.01); C08J 2367/02 (2013.01)

(58) Field of Classification Search
CPC ............. C07D 209/48; C08G 63/6856; C08G 73/1067; C08G 73/16; C08J 2367/02; C08J 5/18; D01F 6/84
See application file for complete search history.

(56) References Cited

U.S. PATENT DOCUMENTS

| | | | |
|---|---|---|---|
| 3,448,150 | A | 6/1969 | Farrissey, Jr. |
| 3,494,933 | A | 2/1970 | Farrissey, Jr. |
| 3,536,670 | A | 10/1970 | Aelony |
| 3,917,892 | A | 11/1975 | Kawaguchi |
| 4,205,157 | A | 5/1980 | Duh |
| 4,578,166 | A | 3/1986 | Uno |
| 4,605,728 | A | 8/1986 | Tung |
| 4,769,444 | A | 9/1988 | Joswig |
| 4,902,771 | A | 2/1990 | Sugawara |
| 4,963,644 | A | 10/1990 | Duh |
| 5,162,455 | A | 11/1992 | Greene |
| 5,288,876 | A | 2/1994 | Greber |
| 5,391,694 | A | 2/1995 | Duh et al. |
| 9,074,052 | B2 | 7/2015 | Sankey |
| 9,096,724 | B2 | 8/2015 | Sankey |
| 9,637,588 | B2 | 5/2017 | Sankey |
| 9,840,590 | B2 | 12/2017 | Sankey et al. |
| 2005/0171326 | A1 | 8/2005 | Edwards |
| 2007/0225410 | A1 | 9/2007 | Edwards |
| 2009/0259000 | A1 | 10/2009 | Urakami |

FOREIGN PATENT DOCUMENTS

| | | |
|---|---|---|
| CN | 101384430 | 3/2009 |
| EP | 0289955 | 11/1988 |
| EP | 0419400 | 2/1996 |
| EP | 2050789 | 4/2009 |
| EP | 2431177 | 3/2012 |
| GB | 1116379 | 6/1968 |

(Continued)

OTHER PUBLICATIONS

Yang et al. " Preparation and characterization of colorless alternate poly(amide-imide)s based on trimellitic anhydride and m-phenylenediamine", Polymer 40 (1999) 1025-1034.*
S.Jabarin "Crystallization Kinetics of Polyethylene Terephthalate". Journal of Applied Polymer Science, vol. 34, 97-102 (1987).*
Li et al. "Poly(ethylene terephthalate co ethylene isophthalate)—relationship between physical roperties and chemical structures " European Polymer Journal 35 (1999), pp. 1607-1610.*
Hisao et al "Structure-property study of polyimides derived from MDA and BPDA dianhydrides with structurally different diamines", European Polymer Journal 38 (2002) 815-828.*

(Continued)

*Primary Examiner* — Ling Siu Choi
*Assistant Examiner* — Gennadiy Mesh
(74) *Attorney, Agent, or Firm* — RatnerPrestia

(57) ABSTRACT

Disclosed herein are film, fiber, molding composition and molded article including copolyesters that exhibit improved heat-resistance and thermo-mechanical stability. The copolyester is derived from an aliphatic glycol, an aromatic dicarboxylic acid selected from naphthalene dicarboxylic acid and terephthalic acid, and 5-50 mol % (based on 100 mole % of all glycols) of an additional monomer, bis(2-hydroxyalkyl)-2,2'-(1,4-phenylene)bis(1,3-dioxoisoindoline-5-carboxylate). The aromatic dicarboxylic acid is at least one of naphthalene dicarboxylic acid and terephthalic acid and the aliphatic glycol is selected from $C_2$, $C_3$ or $C_4$ aliphatic diols. Furthermore, the copolyesters have crystallinity of at least 10%.

17 Claims, No Drawings

(56) References Cited

FOREIGN PATENT DOCUMENTS

| | | |
|---|---|---|
| GB | 1454064 | 10/1976 |
| GB | 1456850 | 11/1976 |
| GB | 2073211 | 10/1981 |
| GB | 2180250 | 3/1987 |
| GB | 2203748 | 10/1988 |
| JP | 4829799 | 4/1973 |
| JP | 4840895 | 6/1973 |
| JP | 4851992 | 7/1973 |
| JP | 5022030 | 3/1975 |
| JP | 50154398 | 12/1975 |
| JP | 54120680 | 9/1979 |
| JP | 56121203 A | 9/1981 |
| JP | 56124120 | 9/1981 |
| JP | 6166314 | 4/1986 |
| JP | H01009866 A | 1/1989 |
| JP | H01225627 A | 9/1989 |
| JP | H01225677 A | 9/1989 |
| JP | 03266628 | 11/1991 |
| JP | 3271272 | 12/1991 |
| JP | 04180939 | 6/1992 |
| JP | 04259534 | 9/1992 |
| JP | H07500132 A | 1/1995 |
| JP | 11228695 | 8/1999 |
| JP | 2004189768 | 7/2004 |
| JP | 2005314601 | 11/2005 |
| JP | 2006160940 | 6/2006 |
| JP | 2007146098 | 6/2007 |
| JP | 2008001877 | 1/2008 |
| JP | 2009525895 A | 7/2009 |
| JP | 2012054289 A | 3/2012 |
| WO | 03022575 | 3/2003 |
| WO | 2005073272 | 8/2005 |
| WO | 2006104243 | 2/2006 |
| WO | 2007014309 | 2/2007 |
| WO | 2007091090 A1 | 8/2007 |
| WO | 2009016388 | 2/2009 |
| WO | 2009127842 | 10/2009 |
| WO | 2009150424 | 12/2009 |
| WO | 2013093446 | 6/2013 |
| WO | 2013093448 | 6/2013 |
| WO | 2014096763 | 6/2014 |
| WO | 2014195714 | 12/2014 |
| WO | 2014202960 | 12/2014 |
| WO | 2014202961 | 12/2014 |
| WO | 2015052492 | 4/2015 |
| WO | 2015193682 | 12/2015 |

OTHER PUBLICATIONS

B. Wunderlich, Macromoleucular Physics, Academic Press, New York, (1980).
D. Lee et al., "Synthesis and Properties of Thermotropic Liquid Crystalline Polyurethane Elastomers (II): Effect of Structure of Chain Extender Containing Imide Unit," Korea Polymer Journal, 1999, (7), 6, 356-363.
D. Lee et al., "Synthesis and Properties of Thermotropic Liquid Crystalline Polyurethane Elastomers (III)—Effect of One or Two-step Polymerization Methods," Journal of the Korean Fiber Society, 1999, (36), 12, 873-880, abstract only.
Database Chemcats—Apr. 11, 2011, XP002690776, Accession No. 2042761681.
Database Chemcats—Apr. 11, 2011, XP002690777, Accession No. 0065728262.
Entire patent prosecution history of U.S. Appl. No. 14/366,511, filed, Jun. 18, 2014, entitled, "Copolyesterimides of Poly(Alkylene Naphthalate)s Having High Glass Transition Temperature and Film Made Therefrom.".
Entire patent prosecution history of U.S. Appl. No. 14/366,915, filed, Jun. 19, 2014, entitled, "Copolyesterimides of Poly(Alkylene Terephthalate)s Having High Glass Transition Temperature and Film Made Therefrom .".
Entire patent prosecution history of U.S. Appl. No. 14/896,039, filed, Dec. 4, 2015, entitled, "Copolyesterimides Derived From N,N'-Bis-(Hydroxyalkyl)-Pyromellitic Diimide and Films Made Therefrom.".
Entire patent prosecution history of U.S. Appl. No. 14/898,614, filed, Dec. 15, 2015, entitled, "Copolyesterimides Derived From N, N'-Bis-(Hydroxyalkyl)-benzophenone-3,3',4,4'-Tetracarboxylic Dimide and Films Made Therefrom.".
Entire patent prosecution history of U.S. Appl. No. 14/898,618, filed, Dec. 15, 2015, entitled, "Copolyesterimides Derived From N,N'-Bis-(Hydroxyalkyl)-3,3',4,4'-Diphenylsulfonete Tracarboxylic Diimide and Films Made Therefrom .".
International Preliminary Report for Patentability dated Jun. 24, 2014 for International Application No. PCT/GB2012/053173.
International Preliminary Report on Patentability and Written Opinion of the International Searching Authority for International Application No. PCT/GB2014/051740 dated Dec. 8, 2015.
International Preliminary Report on Patentability dated Dec. 3, 2015 for International Application No. PCT/GB2014/052995.
International Preliminary Report on Patentability for International Application No. PCT/GB2014/051853 dated Sep. 10, 2015.
International Preliminary Report on Patentability dated Jun. 24, 2014 for International Application No. PCT/GB2012/053171.
International Search Report dated Jan. 7, 2015 for International Application No. PCT/GB2014/052995.
International Search Report for International Application No. PCT/GB2012/053171 dated Mar. 5, 2013.
International Search Report for International Application No. PCT/GB2012/053173 dated Feb. 15, 2013.
International Search Report for International Application No. PCT/GB2014/051740 dated Aug. 21, 2014.
International Search Report for International Application No. PCT/GB2014/051852 dated Aug. 22, 2014.
International Search Report for International Application No. PCT/GB2014/051853 dated Aug. 26, 2014.
K. Faghihi "New optical active poly(amide-imide)s derived from N,N'-(4,4-diphthaloyl)-bis-L-leucine and hydantoin derivatives: Synthesis and properties," Chinese chemical letters, 2009, (20), 10, 1153-1156.
L.S. Park, et al., "Melt polymerization of copoly(ethylene terephthalate-imide)s and thermal properties," 1996, pp. 2059-2067, vol. 60(12), Journal of Applied Polymer Science.
Lee, W.F., et al., "Various properties of diimide-diacid-modified saturated polyesters," Apr. 4, 1994, pp. 69-75, vol. 52(1), Journal of Applied Polymer Science.
M. Sato, et al., "Preliminary communication Thermotropic semi-rigid copoly(imide-carbonate)s composed of 3,4,3",4"-p-terphenyltetracarboxdi-imide and 3,4,3',4'-biphenyltetracarboxdi-imide rings," Liquid crystals, 2000, (27), 8, pp. 1123-1128.
M. Sato et al., "Liquid Crystalline and Fluorescent Properties of Semi-Rigid Poly(ester imide)s Derived from Bismethyl Ester and Bisalcohol Derivatives of 3,3,4,4-Biphenyltetracarboxdimide," Polymer Journal, vol. 34, No. 3, pp. 158-165 (Mar. 2002).
M. Sato et al., "Thermotropic liquid-crystalline aromatic-aliphatic polyimides, 6a) Poly(ester-imide)s based on 3, 4:3', 4'-biphenyldicarboximide," Macromolecular Rapid Communications, vol. 15, Mar. 1, 1994, pp. 203-209, ISSN:1022-1336.
M. Sato et al., "Thermotropic liquid crystalline aromatic-aliphatic polyimides-5. Preparation and properties of homo- and copoly(imide-carbortates)s based on benzophenonetetracarboxylic diimide and biphenyl units," 1996, pp. 639-645, vol. 32(5), European Polymer Journal.
M. Sato et al.; "Preparation and thermal properties of semi-rigid homopoly (imide-carbonate)s composed of symmetric aromatic diimide units using diphenyl carbonate," European Polymer Journal, Pergamon press ltd. Oxford, GB, vol. 37, No. 6, Jun. 1, 2001, pp. 1151-1157.
Notice of Allowance dated May 21, 2015 in U.S. Appl. No. 14/366,915.
S. Cheng, et al., "Glass Transition and Melting Behavior of Poly-(ethylene-2, 6-naphthalenedicarboxylate)," Macromolecules 1988, vol. 21, No. 3, pp. 789-797.

(56) References Cited

OTHER PUBLICATIONS

Sun et al., "Study on the Thermotropic Liquid Crystalline Polycarbonates IV. Synthesis and Properties of Liquid Crystalline Poly(imide Carbonate)s", Journal of Polymer Science, 1994, vol. 31(16, pp. 3039-3046).
T. Hirata, et al., "Thermotropic liquid-crystalline aromatic-aliphatic polyimides, 3a) Poly(imide-carbonate)s composed of 3, 4:3', 4'-biphenyldicarboximide," Macromol. Chem. Phys., 1994, vol. 195, pp. 1611-1622.
USPTO Structure Search, May 2015.
Written Opinion dated Jan. 7, 2015 for International Application No. PCT/GB2014/052995.
Written Opinion of the International Preliminary Examining Authority for International Application No. PCT/GB2014/051853 dated Jun. 5, 2015.
Written Opinion of the International Searching Authority for International Application No. PCT/GB2014/051852 dated Aug. 22, 2014.
Xu Hao et al., "Application status and development trend of novel polyester products," China Synthetic Fiber Industry, vol. 31, No. 4, pp. 45-48, Aug. 2008.
Zhang Congrong, "Application of Polyester Film in Foreign Countries," Shanghai Packaging, No. 1, pp. 29, Feb. 2002.
Non Final Office Action for U.S. Appl. No. 15/027,503, dated Aug. 3, 2016, 16pages.
Notice of Allowance for U.S. Appl. No. 14/898,618, dated Jul. 5, 2016, 18 pages.
Chinese Office Action for Chinese Application No. 2014800351468, dated May 13, 2016, 4 pages.
European Examination Report for European Application No. 14732346.3, dated Jul. 20, 2016 4 pages.
European Examination Report for European Application No. 14781646.6, dated Jul. 25, 2016, 5 pages.
GB Search Report for GB Application No. 1411044.9, dated Dec. 23, 2014, 4 pages.
International Search Report and Written Opinion of the International Searching Authority for International Application No. PCT/GB2015/051795, 8 pages.
Notce of Allowance for U.S. Appl. No. 15/027,503, dated Mar. 13, 2017, 11 pages.
Suzuki et al., Synthesis and Properties of Polyesterimides Containing a Bicyclo-octene Ring, Die Angewandte Makromolekulare Chemie vol. 66 , Jan. 1978, pp. 181-191.
Non Final Office Action for U.S. Appl. No. 14/898,614, dated Feb. 23, 2017, 23 pages.
Non Final Office Action for U.S. Appl. No. 14/898,614, dated Jun. 26, 2017.
Notice of Allowance for U.S. Appl. No. 14/898,614, dated Oct. 24, 2017, 17 pages.
Non Final Office Action for U.S. Appl. No. 14/896,039, dated Nov. 30, 2017, 39 pages.
Yasufuku (Application of poly(ethylene naphthalate) films to electrical and audio-visual uses in Japan. IEEE Electrical Insulation Magazine. vol. 12, Issue 6, Nov.-Dec. 1996, pp. 8-14.
Japanese Office Action for Application No. 2016-517684, dated Jun. 4, 2018 with translation, 11 pages.
Final Office Action for U.S. Appl. No. 14/896,039, dated Mar. 28, 2018, 21 pages.
"The Synthesis and Cross-Linking of a PET Copolyester", Journal of Adhesion Society of Japan with English Abstract, vol. 26, No. 1, pp. 4-13.
Changming, "Chemical Basics of Polymer Insulation Materials", First Edition, Harbin Institute of Technology Press, 2007 with translation, 7 pages.
Non Final Office Action for U.S. Appl. No. 15/812,208, dated Dec. 10, 2018, 32 pages.
Hu et al., "Biaxially Oriented Poly(Ethylene 2,6-Naphthalene) Films: Manufacture, Properties and Commercial Applications, Chapter 10", Modern Polyesters, Chemistry and Technology of Polyesters and Copolyesters, 2003, pp. 335-360.
Non Final Office Action for U.S. Appl. No. 14/896,039, dated Mar. 29. 2019, 29 pages.

* cited by examiner even approximate identity.
COPOLYESTERIMIDES COMPRISING BIS(2-HYDROXYALKYL)-2,2'-(1,4-PHENYLENE)BIS(1,3-DIOXOISOINDOLINE-5-CARBOXYLATE) AND ARTICLES MADE THEREFROM This application is a National Phase filing of International Application No. PCT/GB2015/051795, filed 19 Jun. 2015, and claims priority benefit of GB Application No. 1411044.9, filed 20 Jun. 2014, the entirety of which applications is incorporated herein by reference for all purposes.

FIELD OF THE INVENTION

The present invention is concerned with novel polyesters and films and other articles made therefrom, and methods for their synthesis. In particular, the present invention is concerned with novel copolymers of aromatic carboxylic acids, particularly copolymers of poly(alkylene naphthalate)s and copolymers of poly(alkylene terephthalates), which exhibit improved heat-resistance and thermo-mechanical stability.

BACKGROUND OF THE INVENTION

The glass transition temperature ($T_g$), crystalline melting point ($T_m$) and degree of crystallinity are key parameters in determining the thermo-mechanical properties of polyesters. Previous studies have succeeded in increasing the $T_g$ of thermoplastic polymers, primarily homopolymers, but this has typically been accompanied by a corresponding increase in the $T_m$. Such increases in $T_m$ can be disadvantageous because a thermoplastic polymer should also remain melt-processible (for instance in an extruder), and should preferably remain so under economic conditions (for instance, below about 320° C., preferably below about 300° C., which allows the use of conventional extrusion equipment). At higher processing temperatures, polymer extrusion requires expensive specialist equipment and a great deal of energy, and typically also results in degradation products. The melt-processing temperature should be well below (for instance, at least about 20° C. below) the decomposition temperature of the polymer. In some cases, comonomers have been introduced into polymers in order to increase $T_g$ while retaining $T_m$, but also resulting in convergence of the decomposition temperature and the $T_m$, which leads to the production of degradation products in the melt.

Many attempts have also been made to enhance the glass transition temperature of polyesters by the introduction of more rigid comonomers. However, such comonomers also disrupt the packing of the polymer chains in the crystal lattice, so that while the $T_g$ increases, the $T_m$ and degree of crystallinity typically both decrease as the proportion of comonomer increases, leading ultimately to amorphous materials. In order to fabricate articles from polymeric materials, it is often critical that the polymer exhibit crystallinity to achieve articles with acceptable thermo-mechanical properties.

SUMMARY OF THE INVENTION

Poly(ethylene terephthalate) (PET) is a semi-crystalline copolymer having a glass transition temperature ($T_g$) of 78° C. and a crystalline melting point of ($T_m$) of 260° C. Poly(ethylene naphthalate) (PEN) is a semi-crystalline copolymer having a higher glass transition temperature ($T_g$=120° C.) relative to PET, although their crystalline melting points do not differ greatly ($T_m$=268° C. for PEN). The thermo-mechanical stability of PEN is significantly greater than that of PET. Many of the attempts made to enhance $T_g$ by the introduction of more rigid comonomers have focused on PET, which is significantly cheaper than PEN. There are no commercially available semi-crystalline polyesters with a $T_g$ higher than PEN. Polyether ether ketone (PEEK) is one of the few examples of a high $T_g$ (approximately 143-146° C.) semi-crystalline thermoplastic polymer, and has been used successfully in engineering and biomedical applications. However, PEEK is suitable only for certain types of articles; for instance, it is not suitable for the manufacture of biaxially oriented films. PEEK is also very expensive and has a high crystalline melting point (approximately 350° C.).

An object of the present invention is to provide polyesters which exhibit improved heat-resistance and thermo-mechanical stability. A further object of the present invention is to provide a thermoplastic polymer with high or increased $T_g$ but without increasing $T_m$ to a point where the polymer is no longer melt-processable under economic conditions (i.e. the polymer should remain melt-processable below about 320° C., preferably below about 300° C.). A further object of the present invention is to provide semi-crystalline polyesters which exhibit high $T_g$ as well as high $T_m$. A further object of the present invention is to increase the $T_g$ of a polyester without significantly decreasing its $T_m$ and/or its degree of crystallinity, and preferably without significantly decreasing its decomposition temperature.

As used herein, the term "without significantly decreasing the $T_m$" means that the $T_m$ decreases by no more than 10%, preferably no more than 5%.

As used herein, the term "without significantly decreasing the degree of crystallinity", means that the polyester retains a degree of crystallinity which is commercially useful, preferably in the range of from about 10% to about 60%, preferably from about 20 to about 50%.

A further object of the present invention is to provide a copolyester having a $T_g$ which is higher than the corresponding base polyester, without significantly decreasing its $T_m$ and/or its degree of crystallinity and preferably without significantly decreasing its decomposition temperature.

A further object of the present invention is to provide the use of a comonomer suitable for partial substitution of a monomer in a conventional polyester which increases the $T_g$ of said polyester without significantly decreasing its $T_m$ and/or its degree of crystallinity, and preferably without significantly decreasing its decomposition temperature.

DETAILED DESCRIPTION OF THE INVENTION

While the objects of the invention do not exclude an increase in $T_m$, any increase in $T_m$ must not be so large that melt-processing becomes uneconomical and that the $T_m$ and decomposition temperature converge.

The above-mentioned objects of the present invention have, as their underlying objective, the provision of copolyester articles made from a copolyester having a $T_g$ which is higher than the corresponding base polyester, without significantly increasing the $T_m$ to a point where the polymer is no longer melt-processable under economic conditions, particularly without significantly decreasing the degree of crystallinity of the article (in order to achieve acceptable thermo-mechanical properties), and preferably also without significantly decreasing decomposition temperature.

A further object of the invention is to provide the aforementioned copolyesters and articles with good optical properties, in particular high clarity and/or transparency. One of the advantages of PET and PEN in industrial applications, particularly in the manufacture of semi-crystalline oriented films, is their transparency. An object of the present invention is to retain the desirable optical properties of PET and PEN while enhancing heat-resistance and thermo-mechanical stability.

As used herein, the term "copolyester" refers to a polymer which comprises ester linkages and which is derived from three or more types of comonomers. As used herein, the term "corresponding base polyester" refers to a polymer which comprises ester linkages and which is derived from two types of comonomers comprising ester-forming functionalities, and which serves as a comparator for a copolyester which is derived from comonomers comprising the comonomers of the corresponding base polyester. A comonomer comprising ester-forming functionalities preferably possesses two ester-forming functionalities.

As used herein, the term "semi-crystalline" is intended to mean a degree of crystallinity of at least about 5% measured according to the test described herein, preferably at least about 10%, preferably at least about 15%, and preferably at least about 20%.

Accordingly, the present invention provides a copolyester comprising repeating units derived from an aliphatic glycol, an aromatic dicarboxylic acid (preferably selected from terephthalic acid and naphthalene-dicarboxylic acid), and the monomer of formula (I):

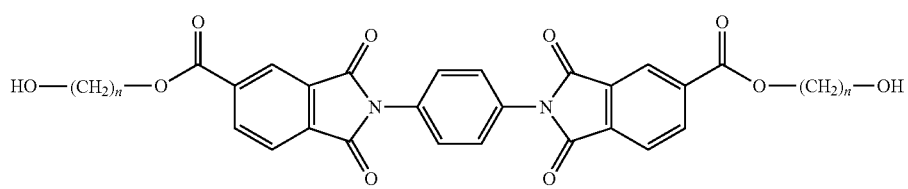

wherein:
$n=2$, 3 or 4, and preferably wherein $n=2$; and
comonomer (I) constitutes a proportion of the glycol fraction of the copolyester.

The monomer of formula (I) is referred to herein as bis(2-hydroxyalkyl)-2,2'-(1,4-phenylene)bis(1,3-dioxoisoindoline-5-carboxylate) (PDOIC). Where $n=2$, the monomer has the formula (II):

melt-processed below 320° C. (preferably below 300° C.) into tough, high strength articles. The copolyesters are also referred to herein as co(polyester-imide)s.

The comonomer (I) constitutes a proportion of the glycol fraction of the copolyester. In a preferred embodiment, the comonomer (I) is present in amounts of no more than about 50 mol % of the glycol fraction of the copolyester, preferably no more than about 40 mol %, preferably no more than about 30 mol %, preferably no more than about 20 mol %, in one embodiment no more than about 15 mol % and in a further embodiment no more than about 10 mol %. Preferably the comonomer is present in an amount of at least about 1 mol %, more preferably at least about 3 mol % (i.e. 3 mol % or greater than 3 mol %), more preferably at least about 4 mol % (i.e. 4 mol % or greater than 4 mol %), more preferably at least about 5 mol % (i.e. 5 mol % or greater than 5 mol %) of the glycol fraction of the copolyester.

Where the aromatic acid is terephthalic acid, the comonomer (I) is preferably present in amounts of no more than about 15 mol %.

In the embodiment where the aromatic acid is naphthalene-dicarboxylic acid, the comonomer (I) may be present in amounts of no more than about 15 mol %.

The inventors have observed that even at low molar fractions of the comonomer (I), small but valuable increases in $T_g$ are observed. For instance, a copolyester comprising only 5 mol % comonomer (I) where $n=2$ exhibits a significant rise in $T_g$, while retaining a good degree of crystallinity.

The aromatic dicarboxylic acid is preferably selected from terephthalic acid and naphthalene-dicarboxylic acid. Other aromatic dicarboxylic acids which may be used in the present invention include isophthalic acid and phthalic acid. The naphthalene-dicarboxylic acid can be selected from

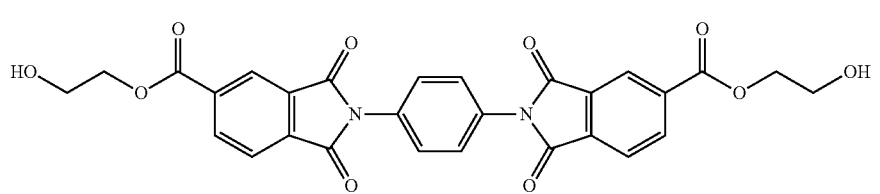

Surprisingly, the present inventors have now found that incorporation of the specific co-monomer (I) into the polyester not only increases the $T_g$ substantially but does so without significant detriment to the crystallinity of articles made therefrom. This is achieved without significantly increasing the $T_m$. The copolyesters described herein are thermoplastic. Copolyesters and articles made therefrom as described herein exhibit semi-crystalline properties. The copolyesters described herein can be readily obtained at high molecular weight. The copolyesters described herein can be 2,5-, 2,6- or 2,7-naphthalene dicarboxylic acid, and is preferably 2,6-naphthalene dicarboxylic acid.

The aliphatic glycol is preferably selected from $C_2$, $C_3$ or $C_4$ aliphatic diols, more preferably from ethylene glycol, 1,3-propanediol and 1,4-butanediol, more preferably from ethylene glycol and 1,4-butanediol, and is most preferably ethylene glycol. The number of carbon atoms in the aliphatic glycol may be the same or different as the number (n) in the comonomer (I), but it is most preferably the same in order to retain crystallinity, particularly in order to retain crystallinity with increasing amounts of comonomer. Thus, the aliphatic glycol preferably has the formula $HO(CH_2)_mOH$, where m=n.

In one embodiment, the aliphatic glycol is 1,4-butanediol and n=4. In a preferred embodiment, the aliphatic glycol is ethylene glycol and n=2.

Copolyesters wherein the acid component is selected from 2,6-naphthalene dicarboxylic acid can be described by formula (III) below:

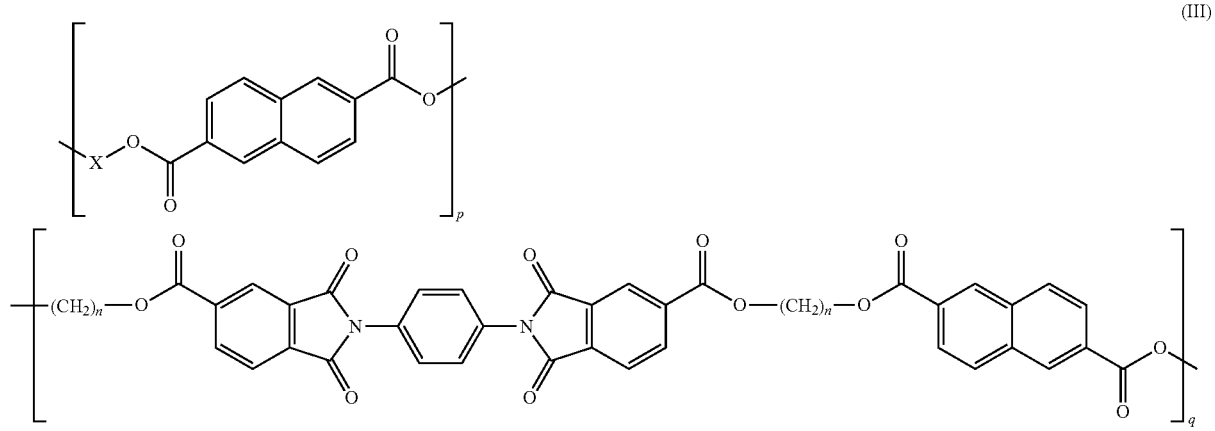

(III)

wherein:
n is as defined for formula (I);
the group X is the carbon chain of said aliphatic glycol;
and p and q are the molar fractions of the aliphatic glycol-containing repeating ester units and the monomer (I)-containing repeating ester units, respectively, as defined hereinabove (i.e. q is preferably no more than 50, and p=100−q).

Copolyesters wherein the acid component is selected from terephthalic acid can be described by formula (IV) below:

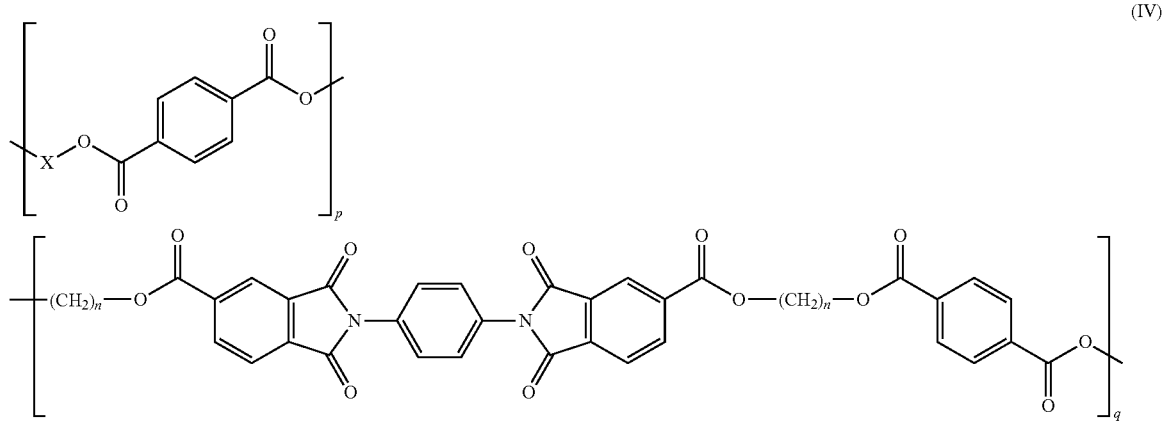

(IV)

wherein n, X, p and q are as described above.

The copolyester may contain more than one type of the aforementioned aliphatic glycols, and/or more than one type of monomer of formula (I) (i.e. a plurality of types of monomer with differing values of n). Preferably, however, the copolyester comprises a single type of the aforementioned aliphatic glycols. Preferably, the copolyester comprises a single type of monomer of formula (I). Preferably, the copolyester comprises a single type of the aforementioned aliphatic glycols, and a single type of monomer of formula (I). Where the copolyester contains more than one type of said aliphatic glycols, then preferably the copolyester comprises a major aliphatic glycol fraction of a single type of said aliphatic glycols, and a minor aliphatic glycol fraction of one or different type(s) of said aliphatic glycols, wherein said one or more different type(s) of said aliphatic glycols constitutes no more than 10 mol %, preferably no more than 5 mol %, preferably no more than 1 mol % of the total glycol fraction. Similarly, where the copolyester contains more than one type of said monomer of formula (I), then preferably the copolyester comprises a major fraction of a single type of said monomer of formula (I), and a minor fraction of one or more different type(s) of said monomer of formula (I), wherein said minor fraction of one or more different type(s) of monomer of formula (I) constitutes no more than 10 mol %, preferably no more than 5 mol %, preferably no more than 1 mol % of the total monomer (I) fraction. The copolyesters may contain minor amounts of other glycols and in a preferred embodiment such other glycols constitute no more than 10 mol %, preferably no more than 5 mol %, preferably no more than 1 mol % of the total glycol fraction, but in order to maximise performance it is preferred that the glycol fraction consists of comonomer (I) and said aliphatic glycol(s) described above.

The copolyesters described herein may contain more than one type of carboxylic acid. In this embodiment, the copolyester comprises a first aromatic dicarboxylic acid, which is preferably terephthalic acid or naphthalene-dicarboxylic acid, as described hereinabove, and one or more additional carboxylic acid(s). The additional carboxylic acid(s) is/are present in minor amounts (preferably no more than 10 mol %, preferably no more than 5 mol %, preferably no more than 1 mol % of the total acid fraction) and is/are different to said first aromatic carboxylic acid. The additional carboxylic acid(s) is/are preferably selected from dicarboxylic acids, preferably from aromatic dicarboxylic acids, for instance including terephthalic acid (where the first aromatic dicarboxylic acid is naphthalene-dicarboxylic acid), naphthalene-dicarboxylic acid (where the first aromatic dicarboxylic acid is terephthalic acid), isophthalic acid, 1,4-naphthalenedicarboxylic acid and 4,4'-diphenyldicarboxylic acid. In this embodiment, the first aromatic dicarboxylic acid may be one isomer of naphthalene-dicarboxylic acid, and the additional dicarboxylic acid(s) may be selected from other isomer(s) of naphthalene-dicarboxylic acid.

Preferably, however, the acid fraction consists of a single aromatic dicarboxylic acid as described hereinabove.

Thus, the copolyester described herein preferably contains only aliphatic glycol, an aromatic dicarboxylic acid (preferably terephthalic acid or naphthalene-dicarboxylic acid) and the monomer of formula (I) defined hereinabove.

The copolyesters described herein can be synthesized according to conventional techniques for the manufacture of polyester materials by condensation or ester interchange, typically at temperatures up to about 310° C. Polycondensation may include a solid phase polymerization (SSP) stage. The solid phase polymerization may be carried out in a fluidized bed, e.g. fluidized with nitrogen, or in a vacuum fluidized bed, using a rotary vacuum drier. Suitable solid phase polymerization techniques are disclosed in, for example, EP-A-0419400 the disclosure of which is incorporated herein by reference. Thus, SSP is typically conducted at a temperature 10-50° C. below the crystalline melting point ($T_m$) of the polymer but higher than the glass transition temperature ($T_g$). An inert atmosphere of dry nitrogen or a vacuum is used to prevent degradation. In one embodiment, the copolyester is prepared using germanium-based catalysts which provide a polymeric material having a reduced level of contaminants such as catalyst residues, undesirable inorganic deposits and other by-products of polymer manufacture. Thus, according to a further aspect of the invention, there is provided a process for preparing a copolyester as defined herein, wherein said process comprises the steps of:

(i) reacting said aliphatic glycol with said aromatic dicarboxylic acid to form a bis(hydroxyalkyl)-ester of said aromatic dicarboxylic acid; and (ii) reacting said bis(hydroxyalkyl)-ester of said aromatic dicarboxylic acid with the monomer (I) under conditions of elevated temperature and pressure in the presence of a catalyst.

In one embodiment, the aliphatic glycol is reacted with the naphthalene dicarboxylic acid to form a bis(hydroxyalkyl)-naphthalate, which is then reacted with the monomer (I) in the desired molar ratios under conditions of elevated temperature and pressure in the presence of a catalyst. In a further embodiment, the aliphatic glycol is reacted with the terephthalic acid to form a bis(hydroxyalkyl)-terephthalate, which is then reacted with the monomer (I) in the desired molar ratios under conditions of elevated temperature and pressure in the presence of a catalyst, as exemplified in Scheme (1) hereinbelow.

The process according to the present invention described hereinabove advantageously allows preparation of the copolyester with high selectivity and high yield. The process advantageously also provides a stable and relatively rapid reaction, facilitating a reliable and reproducible polymerization and allowing scale-up in a safe and economical manner, and also improves the uniformity of the product.

According to a further aspect of the present invention, there is provided a copolyester comprising repeating units derived from an aliphatic glycol, an aromatic dicarboxylic acid, and the monomer of formula (I), wherein comonomer (I) constitutes a proportion of the glycol fraction of the copolyester, and wherein said copolyester is obtainable by the process according to the present invention described hereinabove.

The copolyesters described herein are particularly suitable for use in applications involving exposure to high temperatures and applications which demand high thermo-mechanical performance. The copolyesters may be used to fabricate items in applications in which PEEK has been used, including mechanical components (such as bearings, piston parts, pumps and compressor plate valves); cable insulation; components for ultra-high vacuum applications; advanced biomaterials (including medical implants); and other applications in the aerospace, automotive, teletronic, and chemical process industries. One advantage of the copolyesters described herein over PEEK is that they exhibit $T_g$ values approaching those of PEEK, but with a $T_m$ which is significantly lower. The copolyesters of the present invention can be used in film form or fibre form or in moulding compositions. The copolyesters described herein, particularly the PET-based copolyesters can also be used to manufacture bottles, particularly sterilisable and re-usable bottles.

Surprisingly, the present inventors have found that incorporation of the specific co-monomer (I) into an aromatic polyester (preferably a terephthalate or naphthalate polyester) not only increases the $T_g$ substantially but does so without significant detriment to the crystallinity of articles (particularly films) made therefrom. This is achieved without significantly increasing the $T_m$. Articles (particularly films) made from the copolyesters described herein exhibit semi-crystalline properties.

The copolyesters of the present invention are particularly suitable for film manufacture. Biaxially oriented films in particular are useful as base films for magnetic recording media, particularly magnetic recording media required to exhibit reduced track deviation in order to permit narrow but stable track pitch and allow recording of higher density or capacity of information, for instance magnetic recording media suitable as server back-up/data storage, such as the LTO (Linear Tape Open) format. The copolyesters of the present invention are also suitable for the manufacture of film (preferably biaxially oriented film) for use in electronic and opto-electronic devices (particularly wherein the film is required to be flexible) where thermo-mechanically stable backplanes are critical during fabrication of the finished product, for instance in the manufacture of electroluminescent (EL) display devices (particularly organic light emitting display (OLED) devices), electrophoretic displays (e-paper), photovoltaic (PV) cells and semiconductor devices (such as organic field effect transistors, thin film transistors and integrated circuits generally), particularly flexible such devices.

According to a further aspect of the present invention, there is provided a film comprising a copolyester comprising repeating units derived from an aliphatic glycol, an aromatic dicarboxylic acid, and the monomer of formula (I) defined hereinabove. The film is preferably an oriented film, preferably a biaxially oriented film. Said copolyester is preferably the major component of the film, and makes up at least 50%, preferably at least 65%, preferably at least 80%, preferably at least 90%, and preferably at least 95% by weight of the total weight of the film. Said copolyester is suitably the only polyester used in the film.

Semi-crystalline films of the invention exhibit a degree of crystallinity of at least about 5%, preferably at least about 10%, preferably at least about 15%, preferably at least about 20%, and preferably at least about 25%, measured according to the density method described herein. Thus, the present invention provides films wherein the aromatic dicarboxylic acid (or the first dicarboxylic acid as defined herein) is naphthalene dicarboxylic acid and the degree of crystallinity of the film is at least about 5% (preferably 10%, preferably 15%, preferably 20%, preferably 25%) as calculated from the film density and on the basis of the density of 0% crystalline polyethylene naphthalate (PEN) being 1.325 g/cm$^3$ and the density of 100% crystalline PEN being 1.407 g/cm$^3$; and further provides films wherein the aromatic dicarboxylic acid (or the first dicarboxylic acid as defined herein) is terephthalic acid and the degree of crystallinity of the film is at least about 5% (preferably 10%, preferably 15%, preferably 20%, preferably 25%) as calculated from the film density and on the basis of the density of 0% crystalline polyethylene terephthalate (PET) being 1.335 g/cm$^3$ and the density of 100% crystalline PET being 1.455 g/cm$^3$.

Formation of the film may be effected by conventional extrusion techniques well-known in the art. In general terms the process comprises the steps of extruding a layer of molten polymer at a temperature within an appropriate temperature range, for instance in a range of from about 280 to about 300° C., quenching the extrudate and orienting the quenched extrudate. Orientation may be effected by any process known in the art for producing an oriented film, for example a tubular or flat film process. Biaxial orientation is effected by drawing in two mutually perpendicular directions in the plane of the film to achieve a satisfactory combination of mechanical and physical properties. In a tubular process, simultaneous biaxial orientation may be effected by extruding a thermoplastics polyester tube which is subsequently quenched, reheated and then expanded by internal gas pressure to induce transverse orientation, and withdrawn at a rate which will induce longitudinal orientation. In the preferred flat film process, the film-forming polyester is extruded through a slot die and rapidly quenched upon a chilled casting drum to ensure that the polyester is quenched to the amorphous state. Orientation is then effected by stretching the quenched extrudate in at least one direction at a temperature above the glass transition temperature of the polyester. Sequential orientation may be effected by stretching a flat, quenched extrudate firstly in one direction, usually the longitudinal direction, i.e. the forward direction through the film stretching machine, and then in the transverse direction. Forward stretching of the extrudate is conveniently effected over a set of rotating rolls or between two pairs of nip rolls, transverse stretching then being effected in a stenter apparatus. Stretching is generally effected so that the dimension of the oriented film is from 2 to 5, more preferably 2.5 to 4.5 times its original dimension in the or each direction of stretching. Typically, stretching is effected at temperatures higher than the $T_g$ of the polyester, preferably about 15° C. higher than the $T_g$. Greater draw ratios (for example, up to about 8 times) may be used if orientation in only one direction is required. It is not necessary to stretch equally in the machine and transverse directions although this is preferred if balanced properties are desired.

A stretched film may be, and preferably is, dimensionally stabilized by heat-setting under dimensional support at a temperature above the glass transition temperature of the polyester but below the melting temperature thereof, to induce the desired crystallization of the polyester. During the heat-setting, a small amount of dimensional relaxation may be performed in the transverse direction (TD) by a procedure known as "toe-in". Toe-in can involve dimensional shrinkage of the order 2 to 4% but an analogous dimensional relaxation in the process or machine direction (MD) is difficult to achieve since low line tensions are required and film control and winding becomes problematic. The actual heat-set temperature and time will vary depending on the composition of the film and its desired final thermal shrinkage but should not be selected so as to substantially degrade the toughness properties of the film such as tear resistance. Within these constraints, a heat set temperature of about 150 to 245° C. (typically at least 180° C.) is generally desirable. After heat-setting the film is typically quenched rapidly in order induce the desired crystallinity of the polyester.

In one embodiment, the film may be further stabilized through use of an in-line relaxation stage. Alternatively the relaxation treatment can be performed off-line. In this additional step, the film is heated at a temperature lower than that of the heat-setting stage, and with a much reduced MD and TD tension. The tension experienced by the film is a low tension and typically less than 5 kg/m, preferably less than 3.5 kg/m, more preferably in the range of from 1 to about 2.5 kg/m, and typically in the range of 1.5 to 2 kg/m of film width. For a relaxation process which controls the film speed, the reduction in film speed (and therefore the strain relaxation) is typically in the range 0 to 2.5%, preferably 0.5 to 2.0%. There is no increase in the transverse dimension of the film during the heat-stabilization step. The temperature to be used for the heat stabilization step can vary depending on the desired combination of properties from the final film, with a higher temperature giving better, i.e. lower, residual shrinkage properties. A temperature of 135 to 250° C. is generally desirable, preferably 150 to 230° C., more preferably 170 to 200° C. The duration of heating will depend on the temperature used but is typically in the range of 10 to 40 seconds, with a duration of 20 to 30 seconds being preferred. This heat stabilization process can be carried out by a variety of methods, including flat and vertical configurations and either "off-line" as a separate process step or "in-line" as a continuation of the film manufacturing process. Film thus processed will exhibit a smaller thermal shrinkage than that produced in the absence of such post heat-setting relaxation.

The film may further comprise any other additive conventionally employed in the manufacture of polyester films. Thus, agents such as anti-oxidants, UV-absorbers, hydrolysis stabilizers, cross-linking agents, dyes, fillers, pigments, voiding agents, lubricants, radical scavengers, thermal stabilizers, flame retardants and inhibitors, anti-blocking agents, surface active agents, slip aids, gloss improvers, prodegradents, viscosity modifiers and dispersion stabilizers may be incorporated as appropriate. Such components may be introduced into the polymer in a conventional manner.

For example, by mixing with the monomeric reactants from which the film-forming polymer is derived, or the components may be mixed with the polymer by tumble or dry blending or by compounding in an extruder, followed by cooling and, usually, comminution into granules or chips. Masterbatching technology may also be employed. The film may, in particular, comprise a particulate filler which can improve handling and windability during manufacture, and can be used to modulate optical properties. The particulate filler may, for example, be a particulate inorganic filler (e.g. metal or metalloid oxides, such as alumina, titania, talc and silica (especially precipitated or diatomaceous silica and silica gels), calcined china clay and alkaline metal salts, such as the carbonates and sulphates of calcium and barium).

The thickness of the film can be in the range of from about 1 to about 500 μm, typically no more than about 250 μm, and typically no more than about 150 μm. Particularly where the film of the present invention is for use in magnetic recording media, the thickness of the multilayer film is suitably in the range of from about 1 to about 10 μm, more preferably from about 2 to about 10 μm, more preferably from about 2 to about 7 μm, more preferably from about 3 to about 7 μm, and in one embodiment from about 4 to about 6 μm. Where the film is to be used as a layer in electronic and display devices as described herein, the thickness of the multilayer film is typically in the range of from about 5 to about 350 μm, preferably no more than about 250 μm, and in one embodiment no more than about 100 μm, and in a further embodiment no more than about 50 μm, and typically at least 12 μm, more typically at least about 20 μm.

According to a further aspect of the invention, there is provided an electronic or opto-electronic device comprising the film (particularly the biaxially oriented film) described herein, particularly electronic or opto-electronic devices such as electroluminescent (EL) display devices (particularly organic light emitting display (OLED) devices), electrophoretic displays (e-paper), photovoltaic (PV) cells and semiconductor devices (such as organic field effect transistors, thin film transistors and integrated circuits generally), particularly flexible such devices.

According to a further aspect of the invention, there is provided a magnetic recording medium comprising the film (particularly the biaxially oriented film) described herein as a base film and further comprising a magnetic layer on one surface thereof. The magnetic recording medium includes, for example, linear track system data storage tapes such as QIC or DLT, and, SDLT or LTO of a further higher capacity type. The dimensional change of the base film due to the temperature/humidity change is small, and so a magnetic recording medium suitable to high density and high capacity causing less track deviation can be provided even when the track pitch is narrowed in order to ensure the high capacity of the tape.

According to a further aspect of the invention, there is provided a fibre or moulding composition or moulded article comprising a copolyester comprising repeating units derived from an aliphatic glycol, an aromatic dicarboxylic acid, and the monomer of formula (I) defined hereinabove. The fibre, moulding composition or moulded article may be produced according to conventional techniques in the art. As used herein, the term "moulded articles" includes bottles.

According to a further aspect of the present invention, there is provided a copolyester comprising repeating units derived from an aliphatic glycol, an aromatic dicarboxylic acid and the monomer of formula (I), wherein comonomer (I) constitutes a proportion of the glycol fraction of the copolyester and is preferably present in a range of from about 1 to about 50 mol % of the glycol fraction of the copolyester, and wherein said copolyester is semi-crystalline. The general and specific descriptions hereinabove of copolyesters applies equally to copolyesters of this aspect of the invention. Semi-crystalline copolyesters of the invention exhibit a degree of crystallinity of at least about 5%, preferably at least about 10%, preferably at least about 15%, and preferably at least about 20%, measured according to the standard DSC method described herein. The degree of crystallinity may be increased by annealing or SSP techniques. Annealing is conducted below the crystalline melting point ($T_m$) and above the glass transition temperature ($T_g$) of the polymer, and preferably at 20-80° C. below $T_m$, and preferably from about 160 to about 230° C. For copolyesters where the aromatic carboxylic acid (or the first dicarboxylic acid) is terephthalic acid, preferred annealing temperatures are in the range from about 160 to about 220° C. For copolyesters where the carboxylic acid (or the first dicarboxylic acid) is naphthalene-dicarboxylic acid, preferred annealing temperatures are in the range from about 180 to about 230° C. The annealing time is preferably from about 30 minutes to about 4 hours, preferably from about 1 to about 3 hours, and preferably about 2 hours. Annealing is conducted under an inert atmosphere, preferably dry nitrogen.

The following test methods were used to characterize the properties of the novel compounds disclosed herein.

(i) Glass transition temperature ($T_g$); temperature of cold crystallization ($T_{cc}$), crystalline melting point ($T_m$) and degree of crystallinity ($X_c$) were measured by differential scanning calorimetry (DSC) using a TA Instruments DSC Q2000. Unless otherwise stated, measurements were made according to the following standard test method and based on the method described in ASTM E1356-98. The sample was maintained under an atmosphere of dry nitrogen for the duration of the scan. A flow rate of 50 ml min$^{-1}$ and $T_{zero}$ Al pans were used. Samples of homopolymers and related copolymers (5 mg) were initially heated at 20° C. min$^{-1}$ from 20° C. to 350° C. in order to erase the previous thermal history (1$^{st}$ heating scan). After an isothermal hold at 350° C. for 2 min, samples were cooled at 20° C. min$^{-1}$ to 20° C. (1$^{st}$ cooling scan). Samples were then reheated at 20° C. min$^{-1}$ to 350° C. (2$^{nd}$ heating scan). Values of $T_g$, $T_{cc}$ and $T_m$ were obtained from 2$^{nd}$ heating scans, whereas $T_c$ was obtained from the 1$^{st}$ cooling scans.

The value of $T_g$ was determined as the extrapolated onset temperature of the glass transition observed on the DSC scans (heat flow (W/g) against temperature (° C.)), as described in ASTM E1356-98.

The values of $T_c$, $T_{cc}$ and $T_m$ were determined from the DSC scans as the peak exotherm or endotherm of their respective transitions.

Herein, the degree of crystallinity of the polymer was measured for samples which have been annealed at 200° C. for 2 hours. The annealing of the sample was conducted during a DSC heating cycle using a TA Instruments DSC Q2000 under a nitrogen atmosphere according to the following test method and based on the method described in ASTM E1356-98. A flow rate of 50 ml min$^{-1}$ and $T_{zero}$ Al pans were used. Samples (5 mg) were initially heated at 20° C. min$^{-1}$ from 20° C. to 350° C. in order to erase the previous thermal history (1$^{st}$ heating scan). After an isothermal hold at 350° C. for 2 min, samples were cooled at 20° C. min$^{-1}$ to 200° C. and held at this temperature for 2 h before being cooled at 20° C. min$^{-1}$ to 20° C. (1$^{st}$ cooling scan).

Samples were then reheated at 20° C. min$^{-1}$ to 350° C. (2$^{nd}$ heating scan). The experimental enthalpy of fusion values ($\Delta H_m$) were obtained from the 2$^{nd}$ heating scans. The degree of crystallinity ($X_c$) was calculated according to the equation:

$$X_c = \Delta H_m / \Delta H_m°$$

wherein:
$\Delta H_m$=experimental enthalpy of fusion calculated from the integral of the melting endotherm;
$\Delta H_m°$=theoretical enthalpy of fusion of the corresponding poly(alkylene-carboxylate) homopolymer (i.e. without the co-monomer of formula (I)) at 100% crystallinity. Thus, for copolyesters of the present invention comprising repeating units derived from ethylene glycol, naphthalene-dicarboxylic acid and the co-monomer of formula (I), $\Delta H_m°$ is the theoretical enthalpy of fusion of a 100% crystalline PEN polymer (103 J/g), and for copolyesters of the present invention comprising repeating units derived from ethylene glycol, terephthalic acid and the co-monomer of formula (I), $\Delta H_m°$ is the theoretical enthalpy of fusion of a 100% crystalline PET polymer (140 J/g), as defined in the literature (B. Wunderlich, *Macromolecular Physics*, Academic Press, New York, (1976)).

(ii) Inherent viscosity ($\eta_{inh}$) was determined at 25° C. for 0.1% w/v solutions of the polymer in CHCl$_3$/TFA (2:1) using a Schott-Geräte CT-52 auto-viscometer, with capillary No. 53103. Inherent viscosities were calculated as:

$$\eta_{inh} = \ln[(t_2/t_1)/c]$$

wherein:
$\eta_{inh}$=Inherent Viscosity (dL/g)
$t_1$=Flow time of solvent(s)
$t_2$=Flow time of the polymer solution(s)
c=Concentration of the polymer (g/dL)

Preferably, the inherent viscosity of the copolyesters described herein is at least 0.7 dL/g. Such viscosities are readily obtainable using SSP techniques.

(iii) Degree of crystallinity of the film was measured via measurement of density. The density of film samples was measured using a calibrated calcium nitrate/water density column controlled at a constant 23° C. using a water jacket using the following method. Two 860 ml calcium nitrate solutions of known densities were prepared, filtered and degassed in vacuo for 2 h before being pumped simultaneously into a graduated column tube under hydrostatic equilibrium. The two calcium nitrate solutions of known density are low and high concentration solutions which form a range of densities within the column to encompass the expected densities for the semi-crystalline films of the present invention (corresponding to a degree of crystallinity of from about 0 to about 60%, as defined by the literature densities for the 0 and 100% homopolymers, as noted below for the PET and PEN homopolymers). The concentration of each solution is thus selected on the basis of the aromatic dicarboxylic acid in the polymer (or where more than one dicarboxylic acid is used, on the basis of the first aromatic dicarboxylic acid as defined herein), and the solutions used were as follows.

PET: Low concentration solution: 1.28 g/cm$^3$ (240.80 g calcium nitrate; 860 mL water; 1.71 M molar concentration with respect to calcium nitrate).
High concentration solution: 1.43 g/cm$^3$ (369.80 g calcium nitrate; 860 mL water; 2.62 M calcium nitrate).

PEN: Low concentration solution: 1.32 g/cm$^3$ (275.20 g calcium nitrate; 860 mL water; 1.95 M calcium nitrate).
High concentration solution: 1.41 g/cm$^3$ (352.60 g calcium nitrate, 860 mL water; 2.50 M calcium nitrate).

The density column was calibrated using eight pips of known density which were washed in calcium nitrate solution before being placed in the graduated column. For each pip placed in the column, the volume height of the column was recorded upon reaching a constant level of suspension (after 4 to 5 hours). Separate measurements were taken for each pip to generate a calibration plot of volume height against density. The measurement method was repeated for each film specimen (dimensions 3×5 mm) and three specimens were used for each film sample to generate a mean of the measured volume height, from which the measured density ($\rho_{recorded}$) was obtained from the calibration plot. The degree of crystallinity ($\chi_c$) was then calculated for each sample using Equation (1):

$$\chi_c(\%) = 100\left(\frac{\rho_{recorded} - \rho_{amorphous}}{\rho_{crystalline} - \rho_{amorphous}}\right) \quad (1)$$

where
$\chi_c$=degree of crystallinity (%)
$\rho_{recorded}$=recorded density of polymer (g cm$^{-3}$)
$\rho_{amorphous}$=known density of amorphous homopolymer (o % crystallinity)
$\rho_{crystalline}$=known density of 100% crystalline homopolymer.

(iii) Nuclear magnetic resonance spectroscopy
$^1$H and $^{13}$C NMR spectra were obtained on a Bruker Nanobay 400 MHz spectrometer and referenced to residual solvent resonances or tetramethylsilane. Samples were dissolved in various solvents at room temperature. All values representing chemical shifts, δ, quoted in the assignment of $^1$H and $^{13}$C NMR spectra contain units of ppm.

(iv) Mass spectrometry
Mass spectra were obtained on a LTQ Orbitrap XL with an Accela LC autosampler. Monomer samples were analyzed at a concentration of 1 mg mL$^{-1}$ in DMSO.

(v) Infrared Spectroscopy
IR spectra were recorded on a Perkin Elmer Spectrum 100 FT-IR spectrometer with an Universal Attenuated Total Reflectance accessory. Monomer samples were analyzed as powders and polymeric materials were analyzed as chip.

(vi) Optical Properties
Optical properties of the films are evaluated by measuring total luminance transmission (TLT) and haze (% of scattered transmitted visible light) through the total thickness of the film using a Haze-gard plus spherical hazemeter (BYK Gardner) according to the standard test method ASTM D1003. The optically clear oriented films of the present invention preferably exhibit a haze of no more than about 15%, preferably no more than about 10%, preferably no more than about 5%, preferably no more than about 3%; and/or a TLT of at least about 80%, preferably at least about 85%, and preferably at least about 90%.

The invention is further illustrated by the following examples. It will be appreciated that the examples are for illustrative purposes only and are not intended to limit the invention as described above. Modification of detail may be made without departing from the scope of the invention.

EXAMPLES

An illustrative reaction scheme to prepare copolyesters of the present invention is shown in Scheme 1 below.

solution of 1,2,4-benzenetricarboxylic anhydride (19.20 g, 100.00 mmol) in DMF (50 mL) over 30 mins. The solution was refluxed for a further 1 h, cooled to room temperature, filtered, washed with distilled water and dried in vacuo at 110° C. for 24 h. The intermediate PDOIC product (19.04 g, 83%) was then ground into a fine powder. The intermediate

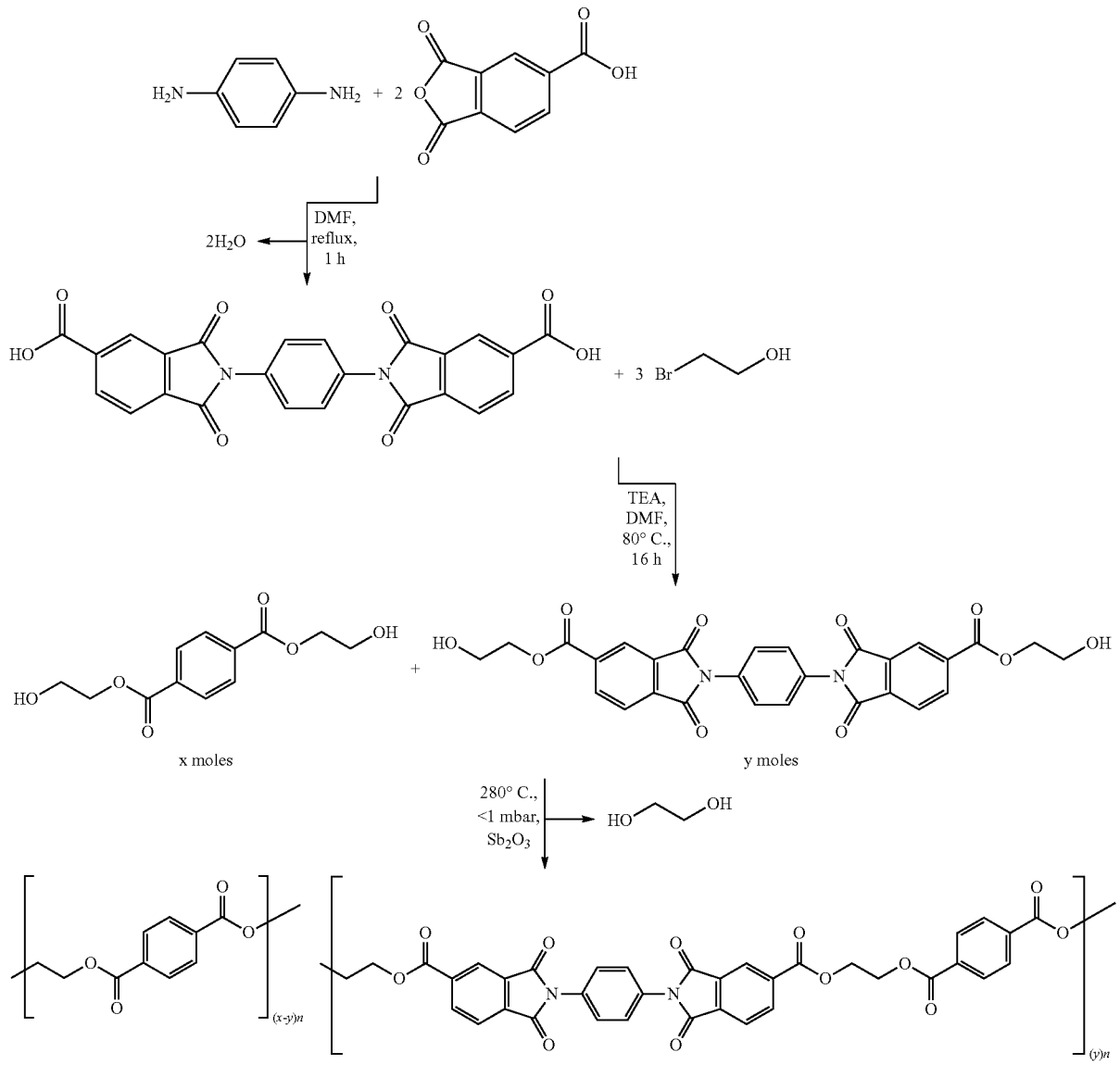

Scheme 1. Synthesis of the bis(hydroxyethyl) comonomer (I) and its copolymerisation via a melt-polycondensation route with bis(hydroxyethyl 2,6-terephthalate) to give a family of co(polyester-imide)s (where n is Scheme 1 is the degree of polymerisation of the overall copolymer).

Example 1

Synthesis of Bis(2-hydroxyethyl)-2,2'-(1,4-phenylene)bis(1,3-dioxoisoindoline-5-carboxylate) (PDOIC; Monomer of Formula I)

A solution of p-phenylene diamine (5.40 g, 50.00 mmol) in DMF (250 mL) was added dropwise to a refluxing PDOIC product (5.00 g, 10.96 mmol) was dissolved in DMF (100 mL). 2-bromoethanol (4.11 g, 32.87 mmol) and triethylamine (3.33 g, 32.87 mmol) were then added to the solution and the reaction was held at 70° C. for 16 h. The solution was cooled to room temperature and suspended in distilled water, filtered, washed with acetone and dried in vacuo at 110° C. for 24 h. The PDOIC product (3.78 g, 63%) was then ground into a fine powder.

Analysis for PDOIC Intermediate

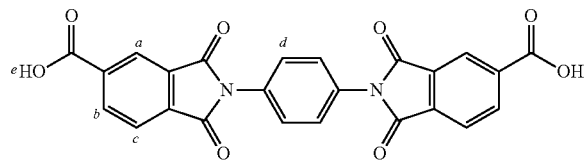 [SMILES: O=C(O)c1ccc2c(c1)C(=O)N(c1ccc(N3C(=O)c4ccc(C(=O)O)cc4C3=O)cc1)C2=O]

Yellow-green powder. m.p. (DSC)=449° C. MS m/z=456.0489 [M+H], calculated 456.0594. $^1$H NMR (400 MHz, d$^6$-DMSO) $\delta_H$ (ppm) 8.42 (2H, s, H$_a$), 8.33 (2H, s, H$_b$), 8.11 (2H, s, H$_c$), 7.64 (4H, s, H$_d$), 3.35 (2H, br, H$_e$). $^{13}$C NMR (100 MHz, CDCl$_3$/TFA (2:1)) $\delta_C$ (ppm) 171.44, 137.30, 133.04, 129.11, 128.66. IR (v$_{max}$ cm$^{-1}$) 2799 (C—H stretch), 1723 (C=O stretch), 1376 (C—O stretch).

Analysis for PDOIC

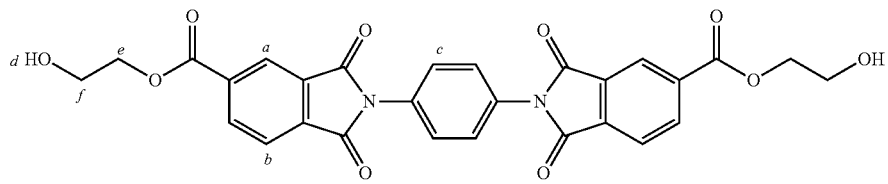 [SMILES: O=C(OCCO)c1ccc2c(c1)C(=O)N(c1ccc(N3C(=O)c4ccc(C(=O)OCCO)cc4C3=O)cc1)C2=O]

Beige powder. m.p. (DSC)=341° C. MS m/z=545.1118 [M+H], calculated 545.1187. $^1$H NMR (400 MHz, d$^6$-DMSO) $\delta_H$ (ppm) 8.46 (4H, s, H$_a$), 8.16 (2H, s, H$_b$), 7.65 (4H, s, H$_c$), 5.08 (2H, s, H$_d$), 4.36 (4H, s, H$_e$), 3.76 (4H, s, H$_f$). $^{13}$C NMR (100 MHz, CDCl$_3$/TFA (2:1)) $\delta_C$ (ppm) 171.39, 169.68, 140.81, 140.56, 140.45, 137.34, 136.31, 133.05, 129.18, 128.85, 72.85, 64.15. IR (v$_{max}$ cm$^{-1}$) 3390 (O—H stretch), 1723 (C=O stretch), 1389 (C—O stretch).

Examples 2 to 9

Synthesis of the Copolyesters

Two series of novel linear poly(ester-imide)s were synthesized by polycondensation between either bis-(2-hydroxyethyl)-terephthalate (BHET) or bis-(2-hydroxyethyl)-2,6-naphthalate (BHEN) and the comonomers of formula (I), in molar amounts of comonomer from about 5 to about 30 mol %. Copolymers containing varying amounts of co-monomer were obtained using Sb$_2$O$_3$ as catalyst. The general polyesterification procedure is as follows, wherein the amounts of reactants used are provided in Tables 1 and 2. A stirred mixture of ester comonomer, PDOIC and Sb$_2$O$_3$ (0.10 g, 0.34 mmol) was poured into a PC rig tube. The PC rig tube was lightly scored on the stem using a Stanley blade to ensure safe extrusion and clamped inside a heating block. After being fitted with a polycondensation head, stirrer guide, air stirrer, delivery side arm, distillate tube inside an ice-filled Dewar flask, thermocouples, optical revolution counter and connected to a gas manifold, the temperature was raised to 235° C. over 1 h under a nitrogen purge. The air stirrer was then started with a pressure of 8.5 psi, with the temperature maintained at 235° C. for 30 min. The nitrogen purge was then stopped, with the system now under vacuum. The pressure was gradually reduced to <5 mm Hg$^{-1}$ as the temperature was increased to 280-310° C. at a rate of 1° C. min$^{-1}$. Once the viscosity of the synthesized polymer had risen sufficiently to lower the stirrer revolution rate by approximately 20-30 rpm, the copolymerization was adjudged to be complete. The vacuum was slowly replaced with a nitrogen purge, allowing the synthesized copolymer to be cooled. The polymer laces extruded from the melt poly-condensation equipment were transparent. The copolymer was then dissolved in a mixed solvent of CHCl$_3$/TFA (2:1) and re-precipitated in MeOH, before being filtered and dried in vacuo at 110° C. for 24 h.

TABLE 1

Reagent masses and feed ratios for PETcoPDOIC copolymers determined by $^1$H NMR.

| | | | PDOIC content ratios | |
|---|---|---|---|---|
| Example | BHET (g) | PDOIC (g) | Feed content (mol %) | Actual content (mol %) |
| 2: PETcoPDOIC-5 | 40.00 | 4.27 | 5 | 5 |
| 3: PETcoPDOIC-10 | 40.00 | 8.55 | 10 | 10 |
| 4: PETcoPDOIC-15 | 20.00 | 7.56 | 15 | 15 |
| 5: PETcoPDOIC-22 | 24.00 | 12.84 | 20 | 22 |
| 6: PETcoPDOIC-28 | 22.00 | 15.66 | 25 | 28 |
| 7: PETcoPDOIC-33 | 20.00 | 18.32 | 30 | 33 |

TABLE 2

Reagent masses and feed ratios for PENcoPDOIC copolymers determined by $^1$H NMR.

| | | | PDOIC content ratios | |
|---|---|---|---|---|
| Example | BHEN (g) | PDOIC (g) | Feed content (mol %) | Actual content (mol %) |
| 8: PENcoPDOIC-5 | 40.00 | 3.57 | 5 | 5 |
| 9: PENcoPDOIC-10 | 40.00 | 7.13 | 10 | 10 |

The analytical data for the copolymers are set out below.
PETcoPDOIC Copolymer Series

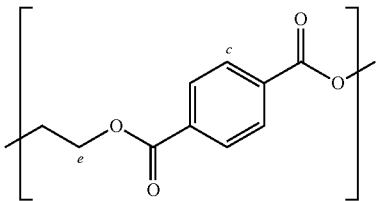

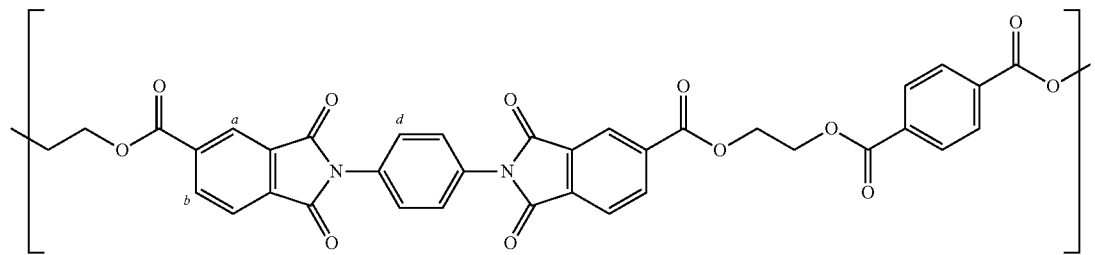

PETcoPDOIC5

$^1$H NMR (400 MHz, CDCl$_3$/TFA (2:1)) δ$_H$ (ppm) 8.74 (2H, s, H$_a$), 8.62 (2H, m, H$_b$), 8.19 (10H, s, H$_c$), 7.67 (4H, s, H$_d$), 4.86 (12H, s, H$_e$). $^{13}$C NMR (100 MHz, CDCl$_3$/TFA (2:1)) δ$_C$ (ppm) 168.05, 136.94, 135.49, 134.93, 133.34, 131.37, 130.86, 129.85, 127.56, 125.64, 124.81, 63.95. T$_g$=91° C., T$_{cc}$=182° C., T$_c$=167° C., T$_m$=240° C. η$_{inh}$ (CHCl$_3$/TFA) (2:1)=0.67 dL g$^{-1}$. IR (ν$_{max}$ cm$^{-1}$) 2961 (C—H stretch), 1713 (C=O stretch), 1238 (C—O stretch).

PETcoPDOIC10

$^1$H NMR (400 MHz, CDCl$_3$/TFA (2:1)) δ$_H$ (ppm) 8.74 (2H, s, H$_a$), 8.63 (2H, s, H$_b$), 8.19 (10H, s, H$_c$), 7.67 (4H, s, H$_d$), 4.86 (12H, s, H$_e$). $^{13}$C NMR (100 MHz, CDCl$_3$/TFA (2:1)) δ$_C$ (ppm) 168.03, 136.94, 135.50, 134.94, 133.28, 131.38, 130.87, 130.03, 127.57, 125.63, 124.81, 63.96. T$_g$=89° C., T$_{cc}$=156° C., T$_c$=163° C., T$_m$=236° C. η$_{inh}$ (CHCl$_3$/TFA) (2:1)=0.37 dL g$^{-1}$. IR (ν$_{max}$ cm$^{-1}$) 2964 (C—H stretch), 1717 (C=O stretch), 1247 (C—O stretch).

PETcoPDOIC15

$^1$H NMR (400 MHz, CDCl$_3$/TFA (2:1)) δ$_H$ (ppm) 8.73 (2H, s, H$_a$), 8.62 (2H, s, H$_b$), 8.18 (10H, s, H$_c$), 7.67 (4H, s, H$_d$), 4.85 (12H, s, H$_e$). $^{13}$C NMR (100 MHz, CDCl$_3$/TFA (2:1)) δ$_C$ (ppm) 168.12, 167.82, 136.97, 135.51, 134.95, 133.28, 131.38, 130.88, 130.03, 127.60, 125.63, 124.82, 65.13, 63.96, 63.27. T$_g$=91° C., T$_c$=204° C., T$_m$=226° C. η$_{inh}$ (CHCl$_3$/TFA) (2:1)=0.49 dL g$^{-1}$. IR (ν$_{max}$ cm$^{-1}$) 2961 (C—H stretch), 1715 (C=O stretch), 1247 (C—O stretch).

PETcoPDOIC22

$^1$H NMR (400 MHz, CDCl$_3$/TFA (2:1)) δ$_H$ (ppm) 8.75 (2H, s, H$_a$), 8.65 (2H, s, H$_b$), 8.19 (10H, s, H$_c$), 7.67 (4H, s, H$_d$), 4.86 (12H, s, H$_e$). $^{13}$C NMR (100 MHz, CDCl$_3$/TFA (2:1)) δ$_C$ (ppm) 168.12, 167.85, 136.98, 135.50, 134.94, 133.28, 131.37, 130.87, 130.02, 127.60, 125.64, 124.84, 65.12, 63.96, 63.28. T$_g$=101° C., T$_c$=213° C., T$_m$=230° C. η$_{inh}$ (CHCl$_3$/TFA) (2:1)=0.37 dL g$^{-1}$. IR (ν$_{max}$ cm$^{-1}$) 2965 (C—H stretch), 1713 (C=O stretch), 1244 (C—O stretch).

PETcoPDOIC28

$^1$H NMR (400 MHz, CDCl$_3$/TFA (2:1)) δ$_H$ (ppm) 8.76 (2H, s, H$_a$), 8.68 (2H, s, H$_b$), 8.21 (10H, s, H$_c$), 7.69 (4H, s, H$_d$), 4.88 (12H, s, H$_e$). $^{13}$C NMR (100 MHz, CDCl$_3$/TFA (2:1)) δ$_C$ (ppm) 168.14, 167.89, 136.99, 135.51, 134.95, 133.28, 131.38, 130.89, 130.03, 127.61, 125.63, 124.82, 65.14, 63.92, 63.28. T$_g$=109° C., T$_c$=219° C., T$_m$=246° C. η$_{inh}$ (CHCl$_3$/TFA) (2:1)=0.32 dL g$^{-1}$. IR (ν$_{max}$ cm$^{-1}$) 2964 (C—H stretch), 1713 (C=O stretch), 1247 (C—O stretch).

PETcoPDOIC33

$^1$H NMR (400 MHz, CDCl$_3$/TFA (2:1)) δ$_H$ (ppm) 8.74 (2H, s, H$_a$), 8.65 (2H, s, H$_b$), 8.19 (10H, s, H$_c$), 7.67 (4H, s, H$_d$), 4.86 (12H, s, H$_e$). $^{13}$C NMR (100 MHz, CDCl$_3$/TFA (2:1)) δ$_C$ (ppm) 168.13, 167.86, 136.97, 135.50, 134.95, 133.28, 131.37, 130.87, 130.03, 127.60, 125.64, 124.85, 65.12, 63.96, 63.28. T$_g$=107° C., T$_c$=210° C., T$_m$=238° C. η$_{inh}$ (CHCl$_3$/TFA) (2:1)=0.34 dL g$^{-1}$. IR (ν$_{max}$ cm$^{-1}$) 2970 (C—H stretch), 1706 (C=O stretch), 1248 (C—O stretch).

PENcoPDOIC Copolymer Series

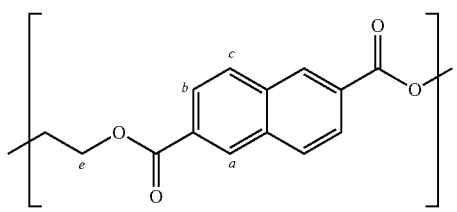

-continued

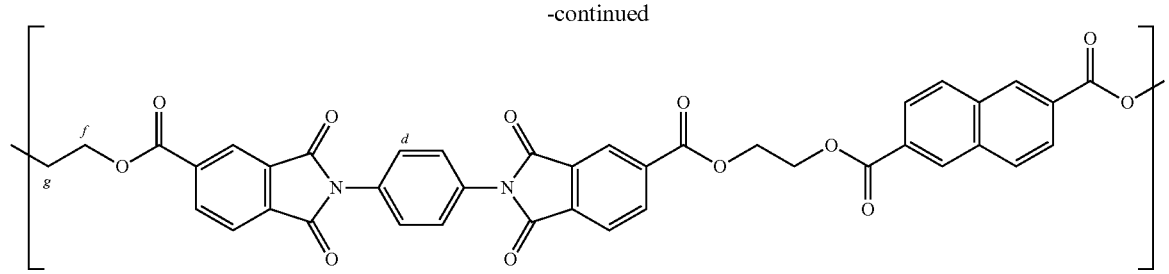

PENcoPDOIC5

$^1$H NMR (400 MHz, CDCl$_3$/TFA (2:1)) $\delta_H$ (ppm) 8.75 (8H, s, H$_a$), 8.17 (6H, s, H$_b$), 8.11 (4H, s, H$_c$), 7.67 (4H, s, H$_d$), 4.96 (4H, s. H$_e$), 4.87 (4H, s, H$_f$), 4.13 (4H, s, H$_g$). $^{13}$C NMR (100 MHz, CDCl$_3$/TFA (2:1)) $\delta_C$ (ppm) 168.89, 136.98, 135.56, 135.02, 133.30, 131.60, 131.39, 130.87, 130.24, 130.05, 128.39, 127.57, 125.76, 124.82, 76.59, 64.03. T$_g$=128° C., T$_c$=220° C., T$_m$=259° C. $\eta_{inh}$ (CHCl$_3$/TFA) (2:1)=0.31 dL g$^{-1}$. IR ($v_{max}$ cm$^{-1}$) 2971 (C—H stretch), 1720 (C=O stretch), 1217 (C—O stretch).

PENcoPDOIC10

$^1$H NMR (400 MHz, CDCl$_3$/TFA (2:1)) $\delta_H$ (ppm) 8.75 (8H, s, H$_a$), 8.17 (6H, s, H$_b$), 8.11 (4H, s, H$_c$), 7.67 (4H, s, H$_d$), 4.96 (4H, s. H$_e$), 4.87 (4H, s, H$_f$), 4.12 (4H, s, H$_g$). $^{13}$C NMR (100 MHz, CDCl$_3$/TFA (2:1)) $\delta_C$ (ppm) 168.96, 136.97, 135.56, 135.02, 133.30, 131.60, 131.39, 130.87, 130.24, 130.05, 128.39, 127.57, 125.76, 124.82, 76.60, 64.03. T$_g$=132° C., T$_c$=200° C., T$_m$=249° C. $\eta_{inh}$ (CHCl$_3$/TFA) (2:1)=0.43 dL g$^{-1}$. IR ($v_{max}$ cm$^{-1}$) 2961 (C—H stretch), 1716 (C=O stretch), 1214 (C—O stretch).

The characterizing data for the Examples are summarized in Tables 3a below. Characterizing data for pure PET or pure PEN as control samples, synthesized in accordance with the procedure described for Examples 2 to 9 but without the inclusion of the comonomer, are shown in Table 3b below.

The enthalpy of fusion and crystallinity data above were obtained using the annealing DSC cycle described hereinabove, and demonstrate surprisingly that good crystallinity is achievable at unexpectedly high molar amounts of comonomer.

TABLE 3a

Thermal and Viscosity Data of the Copolyesterimides

| Ex: Polymer | T$_g$ (° C.) | T$_c$ (° C.) | T$_m$ (° C.) | ΔH$_m$ (J/g) | Xc (%) | Viscosity $\eta_{inh}$ (dL g$^{-1}$) |
|---|---|---|---|---|---|---|
| 2: PETcoPDOIC-5 | 91 | 167 | 240 | 51.20 | 37 | 0.67 |
| 3: PETcoPDOIC-10 | 89 | 163 | 236 | 41.61 | 30 | 0.37 |
| 4: PETcoPDOIC-15 | 91 | 204 | 226 | 28.31 | 20 | 0.49 |
| 5: PETcoPDOIC-22 | 101 | 213 | 230 | 10.06 | 7 | 0.37 |
| 6: PETcoPDOIC-28 | 109 | 219 | 246 | 10.12 | 7 | 0.32 |
| 7: PETcoPDOIC-33 | 107 | 210 | 238 | 7.99 | 6 | 0.34 |
| 8: PENcoPDOIC-5 | 128 | 220 | 259 | 54.83 | 53 | 0.31 |
| 9: PENcoPDOIC-10 | 132 | 200 | 249 | 48.33 | 47 | 0.43 |

TABLE 3b

Thermal and Viscosity Data of PET and PEN

| Ex. | Polymer | T$_g$ (° C.) | T$_c$ (° C.) | T$_m$ (° C.) | ΔH$_m$ (J/g) | Xc (%) | Viscosity $\eta_{inh}$ (dL g$^{-1}$) |
|---|---|---|---|---|---|---|---|
| Control | PET | 75 | 160 | 257 | 44 | 31 | — |
| Control | PEN | 119 | 191 | 267 | 36 | 35 | — |

Samples of the copolymers could be oriented by hot-drawing to multiple times their original dimensions. For example, fibres could be drawn after heating the samples over a hotplate, thereby demonstrating thermoplastic behaviour and drawing capability.

Optically clear biaxially oriented films can be manufactured from the copolymers described above. The polymer is fed to an extruder (single screw; screw speed approx. 80 rpm) at a temperature in the range of 275 to 300° C. A cast film is produced, which is electrostatically pinned and threaded around the casting drum and over the top of the forward draw onto a scrap winder. Once settled, cast samples are collected at a range of casting drum speeds (2, 3 and 5 m\min) to give a range of thicknesses. The cast films are subsequently drawn using a Long Stretcher (supplied by T.M. Long Co., Somerville, N.J.). The Long Stretcher comprises a hydraulically operated stretching head mounted inside a heated oven with a liftable lid. The operation of the stretching mechanism is based upon the relative motion of two pairs of draw bars (one fixed and one moveable, mounted normally to one another). The draw bars are attached to hydraulic rams which control the amount (draw ratio) and speed (draw rate) of the imposed stretching. On each draw bar are mounted pneumatic sample clips attached to a pantograph system. A sample loading system is used to position samples within the pneumatic clips. A cast sample cut to a specific size (11.1×11.1 cm) is located symmetrically on a vacuum plate attached to the end of an arm. The arm is run into the oven and the sample lowered so that it is between the clips. The clips are closed using nitrogen pressure to hold the film and the loading arm withdrawn. The oven is heated to a specified temperature by two plate-heaters. The lid is lowered and air heaters rapidly bring the sample up to a specified temperature. After a suitable preheat time (typically 25-30 seconds), the draw is manually initiated by the operator. A draw rate of from about 2 cm/second to about 5 cm/second is typically used. Simultaneous biaxial draw in perpendicular directions is used in these examples. Suitable processing conditions are given in Table 4 below.

TABLE 4

| Sample | Approx Draw Ratio | Air Heater Temp (° C.) | Plate Heater Temp (° C.) |
|---|---|---|---|
| PEN-based films | 3.5 × 3.5 | 155 | 150 |
| PET-based films | 3.5 × 3.5 | 100-120 | 100-120 |

The films produced on the Long Stretcher are then crystallized using a Laboratory Crystallization Rig and held at specified temperatures (typically 150 to 240° C.) for specified times (typically from 2 to 100 seconds). In this equipment, samples are clamped in a frame which is dropped pneumatically and held between heated platens for a specific time before being rapidly quenched by dropping into iced water.

Crystallinity of film samples is calculated using the density method described herein.

Crystallinity of the PEN-based film samples is calculated using known values for PEN density and crystallinity, on the basis of the following literature data:

Density of 0% crystallinity PEN=1.325 g/cm$^3$
Density of 100% crystallinity PEN=1.407 g/cm$^3$ Crystallinity of the PET-based film samples is calculated using known values for PET density and crystallinity, on the basis of the following literature data:

Density of 0% crystallinity PET=1.335 g/cm$^3$
Density of 100% crystallinity PET=1.455 g/cm$^3$

COMPARATIVE EXAMPLES

A series of four PET-based copolyesterimides was synthesized in accordance with the procedure described above, except that the PDOIC comonomer was replaced with a comonomer showing a degree of structural similarity to PDOIC. The characterizing data for these comonomers and copolyesterimides is provided below.

Comparative Example 1

Bis(2-hydroxyethyl)-2,2'-(1,3-phenylenebis(methylene)) bis(1,3-dioxoisoindoline-5-carboxylate) (TMA-MXDA)

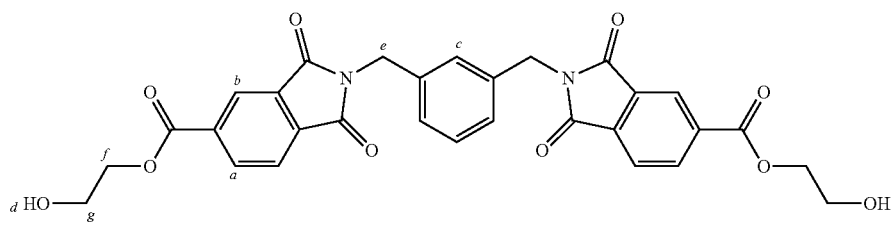 [SMILES: O=C(OCCO)c1ccc2c(c1)C(=O)N(Cc1cccc(CN3C(=O)c4ccc(C(=O)OCCO)cc4C3=O)c1)C2=O]

White powder. m.p. (DSC)=219° C. MS m/z=595.1323 [M+Na], calculated 595.1329. $^1$H NMR (400 MHz, d$^6$-DMSO) $\delta_H$ (ppm) 8.30 (4H, m, H$_a$), 8.00 (2H, m, H$_b$), 7.22 (4H, m, H$_c$), 5.09 (2H, s, H$_d$), 4.76 (4H, s, H$_e$), 4.34 (4H, s, H$_f$), 3.75 (4H, s, H$_g$). $^{13}$C NMR (100 MHz, d$^6$-DMSO) $\delta_C$ (ppm) 166.82, 164.23, 136.66, 135.37, 134.72, 131.91, 128.87, 126.35, 123.59, 123.12, 67.50, 63.52, 58.87. IR ($v_{max}$ cm$^{-1}$) 3363 (O—H stretch), 2957 (C—H stretch), 1710 (C=O stretch), 1252 (C—O stretch).

Comparative Example 2

2-Hydroxyethyl-2-(4-(4-(5-((2-hydroxyethoxy)carbonyl)-1,3-dioxoisoindolin-2-yl)benzyl)phenyl)-1,3-dioxoisoindoline-4-carboxylate (TMA-MDA)

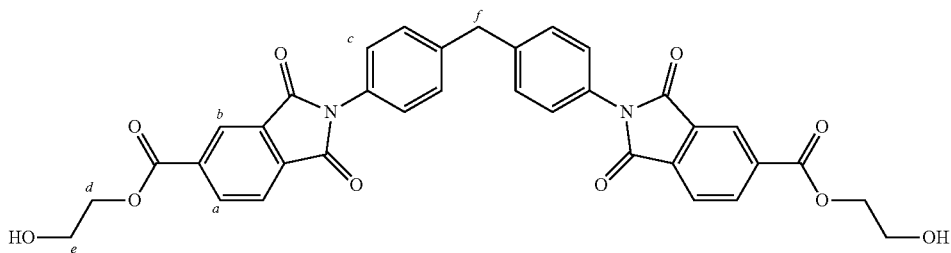 [SMILES: O=C(OCCO)c1ccc2c(c1)C(=O)N(c1ccc(Cc3ccc(N4C(=O)c5ccc(C(=O)OCCO)cc5C4=O)cc3)cc1)C2=O]

Off-yellow powder. m.p. (DSC)=230° C. MS m/z=635.1659 [M+H], calculated 635.1587. $^1$H NMR (400 MHz, d$^6$-DMSO) $\delta_H$ (ppm) 8.46 (4H, m, H$_a$), 8.11 (2H, m, H$_b$), 7.43 (8H, m, H$_c$), 4.93 (2H, m, H$_d$), 4.37 (4H, m, H$_e$), 3.77 (4H, m, H$_f$). $^{13}$C NMR (100 MHz, d$^6$-DMSO) $\delta_C$ (ppm) 162.31, 137.03, 134.97, 131.37, 130.10, 128.10, 127.04, 125.79, 124.71, 67.36, 40.80. IR ($v_{max}$ cm$^{-1}$) 3344 (O—H stretch), 1708 (C=O stretch), 1208 (C—O stretch).

Comparative Example 3

Bis(2-hydroxyethyl)-2,2'-(ethane-1,2-diyl)bis(1,3-dioxoisoindoline-5-carboxylate) (TMA-EDA)

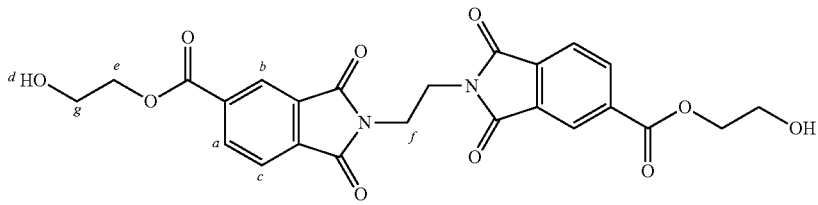 [SMILES: O=C(OCCO)c1ccc2c(c1)C(=O)N(CCN1C(=O)c3ccc(C(=O)OCCO)cc3C1=O)C2=O]

White powder. m.p. (DSC)=220° C. MS m/z=519.1006 [M+Na], calculated 519.1016. $^1$H NMR (400 MHz, d$^6$-DMSO) $\delta_H$ (ppm) 8.37 (2H, s, H$_a$), 8.29 (2H, s, H$_b$), 7.99 (2H, s, H$_c$), 5.05 (2H, s, H$_d$), 4.32 (4H, s, H$_e$), 3.89 (4H, s, H$_f$), 3.71 (4H, s, H$_g$). $^{13}$C NMR (100 MHz, d$^6$-DMSO) $\delta_C$ (ppm) 167.00, 164.33, 135.48, 135.27, 134.83, 131.78, 123.61, 123.25, 67.51, 58.83, 36.46. IR ($v_{max}$ cm$^{-1}$) 3424 (O—H stretch), 2947 (C—H stretch), 1691 (C=O stretch), 1289 (C—O stretch).

Comparative Example 4

Bis(2-hydroxyethyl)-2,2'-(1,3-phenylene)bis(1,3-dioxoisoindoline-5-carboxylate) (MDOIC)

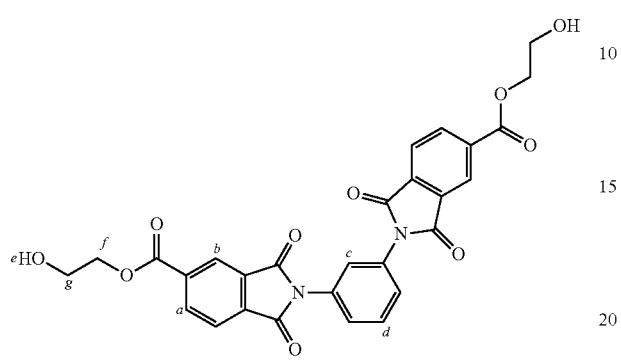

Yellow powder. m.p. (DSC)=190° C. MS m/z=567.1007 [M+Na], calculated 567.1016. $^1$H NMR (400 MHz, d$^6$-DMSO) $\delta_H$ (ppm) 8.46 (4H, m, H$_a$), 8.16 (2H, d, J=8.0 Hz, H$_b$), 7.74 (1H, t, J=8.0 Hz, H$_c$), 7.62 (3H, t, J=8.0 Hz, H$_d$), 5.09 (2H, s, H$_e$), 4.38 (4H, s, H$_f$), 3.77 (4H, s, H$_g$). $^{13}$C NMR (100 MHz, CDCl$_3$:TFA (2:1)) $\delta_C$ (ppm) 166.04, 164.42, 135.51, 135.26, 135.17, 132.13, 132.07, 129.28, 127.16, 125.94, 123.90, 123.55, 67.57, 58.88. IR ($v_{max}$ cm$^{-1}$) 3291 (O—H stretch), 2946 (C—H stretch), 1709 (C=O stretch), 1252 (C—O stretch).

For each of the above comonomers, copolyesterimides were prepared using 10 mol % comonomer. The copolyesterimides were characterized thermally as described hereinabove, and the results are shown in Table 5 below. The copolyesterimides of the comparative examples exhibit no melt-crystallization temperature (Tc) detectable on the first cooling scan, which is reflected in the loss of substantially all crystallinity as represented by the melting peak measured on the second heating scan. The experimental data therefore demonstrate that the PDOIC copolymers unexpectedly retain semi-crystalline behaviour, in comparison with monomers exhibiting structural similarity.

TABLE 5

Thermal property data for copolyesterimide comparative examples

| Polymer | | Tg (° C.) | Tc (° C.) | ΔHc (J g$^{-1}$) | Tm (° C.) | ΔHm (J g$^{-1}$) |
|---|---|---|---|---|---|---|
| C. Ex. 1 | PETcoTMA-MXDA10 | 100 | N/A | N/A | 229 | 3.06 |
| C. Ex. 2 | PETcoTMA-MDA10 | 112 | N/A | N/A | N/A | N/A |
| C. Ex. 3 | PETcoTMA-EDA10 | 99 | N/A | N/A | 228 | 1.96 |
| C. Ex. 4 | PETcoTMA-MDOIC10 | 99 | N/A | N/A | N/A | N/A |

The invention claimed is:

1. A semi-crystalline copolyester derived from an aliphatic glycol, an aromatic dicarboxylic acid, and the monomer of formula (I):

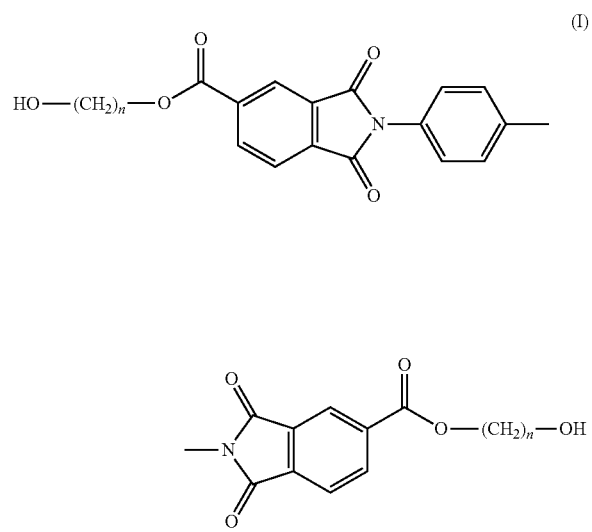

wherein n=2, 3 or 4, and wherein the monomer (I) constitutes from 5 to 20 mol % of the glycol fraction of the copolyester, wherein the aromatic dicarboxylic acid is selected from naphthalene dicarboxylic acid and terephthalic acid, wherein the aliphatic glycol is selected from C$_2$, C$_3$ or C$_4$ aliphatic diols, and wherein said semi-crystalline copolyester exhibits a degree of crystallinity of at least 10%.

2. The copolyester according to claim 1 wherein the monomer (I) is present in amounts of no more than 15 mol % of the glycol fraction of the copolyester.

3. The copolyester according to claim 1 wherein the aliphatic glycol is ethylene glycol.

4. The copolyester according to claim 1 wherein the number of carbon atoms in the aliphatic glycol is the same as the number (n) in monomer (I).

5. The copolyester according to claim 1 wherein n=2.

6. The copolyester according to claim 1 wherein the aromatic dicarboxylic acid is 2,6-naphthalene dicarboxylic acid.

7. The copolyester according to claim 1 which has formula (III):

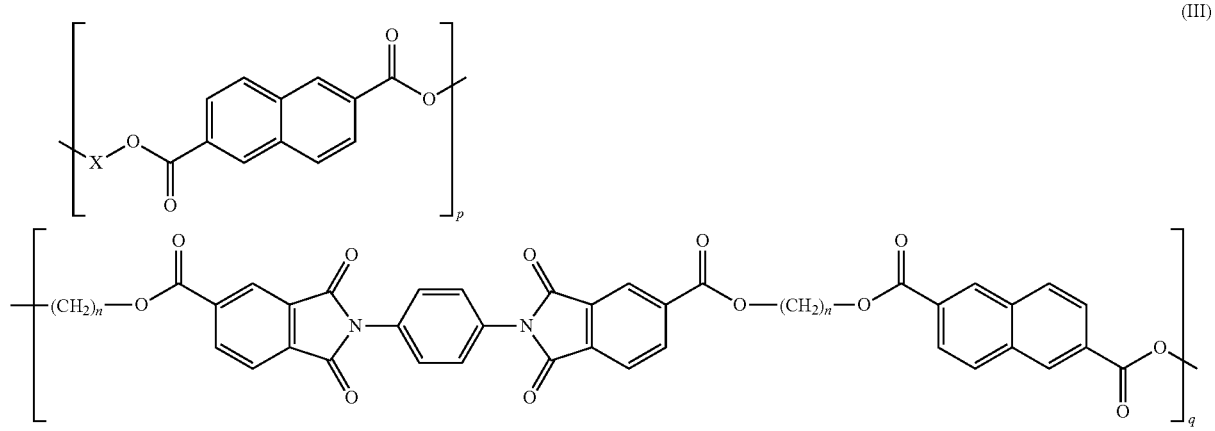

wherein:
n=2, 3 or 4;
the group X is the carbon chain of said aliphatic glycol; and
p and q are the molar fractions of the aliphatic glycol-containing ester units and the monomer (I)-containing ester units, respectively;
wherein q is from 5 to 20 and p is 100-q.

8. The copolyester according to claim 1 wherein the aromatic dicarboxylic acid is terephthalic acid.

9. The copolyester according to claim 1 wherein the aromatic dicarboxylic acid is terephthalic acid and the copolyester has formula (IV):

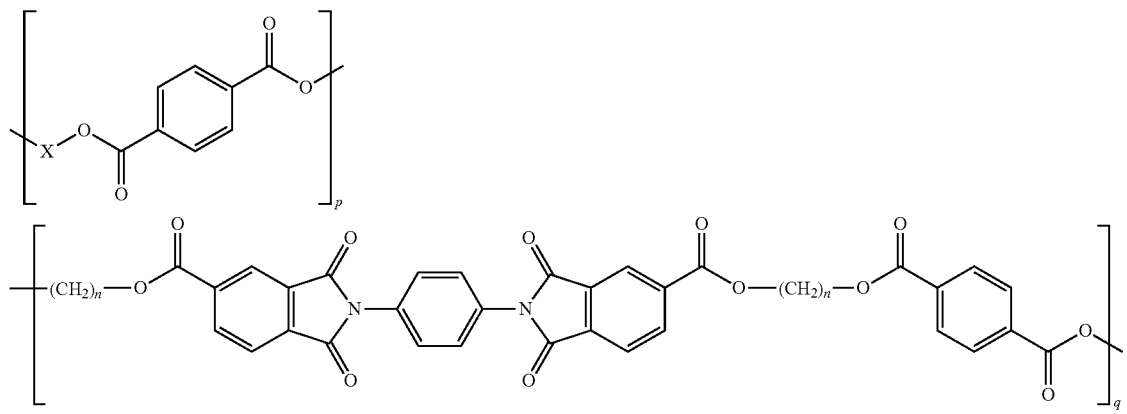

wherein:
n=2, 3 or 4;
the group X is the carbon chain of said aliphatic glycol; and
p and q are the molar fractions of the aliphatic glycol-containing repeating ester units and the monomer (I)-containing repeating ester units, respectively wherein q is from 5 to 20 and p is 100-g.

10. A semi-crystalline polyester film comprising a copolyester according to claim 1, wherein said semi-crystalline polyester film exhibits a degree of crystallinity of at least 10%.

11. The polyester film according to claim 10 which is an oriented film.

12. The film according to claim 11 wherein said oriented film exhibits a haze of no more than 10% and/or a Total Luminance Transmission of at least 80%, as measured by ASTM, D1003.

13. The film according to claim 10 wherein said aromatic dicarboxylic acid is naphthalene dicarboxylic acid and the degree of crystallinity of the film is at least 10% as calculated from the film density and on the basis of the density of 0% crystalline polyethylene naphthalate (PEN) being 1.325 g/cm$^3$ and the density of 100% crystalline PEN being 1.407 g/cm$^3$; or wherein said aromatic dicarboxylic acid is terephthalic acid and the degree of crystallinity of the film is at least about 10% as calculated from the film density and on the basis of the density of 0% crystalline polyethylene terephthalate (PET) being 1.335 g/cm$^3$ and the density of 100% crystalline PET being 1.455 g/cm$^3$.

14. A fibre or moulding composition or moulded article comprising a copolyester according to claim 1.

15. The polyester film according to claim 10 which is a biaxially oriented film.

16. The copolyester according to claim 1 wherein said copolyester exhibits a degree of crystallinity of at least 15%.

17. The copolyester according to claim 1 wherein said copolyester exhibits a degree of crystallinity of, at least 20%.

\* \* \* \* \*

UNITED STATES PATENT AND TRADEMARK OFFICE
CERTIFICATE OF CORRECTION

PATENT NO. : 10,450,411 B2  
APPLICATION NO. : 15/315567  
DATED : October 22, 2019  
INVENTOR(S) : Stephen William Sankey et al.

Page 1 of 1

It is certified that error appears in the above-identified patent and that said Letters Patent is hereby corrected as shown below:

In the Claims

In Column 29, Lines 61 and 62, in Claim 9:
"containing repeating ester units" should read --containing ester unit--

In Column 29, Line 63, in Claim 9:
"p is 100-g." should read -- -p is 100-q.--

In Column 30, Line 26, in Claim 12:
"ASTM, D1003." should read --ASTM D1003.--

Signed and Sealed this  
Seventh Day of January, 2020

Andrei Iancu  
*Director of the United States Patent and Trademark Office*